United States Patent
Mariaulle et al.

(10) Patent No.: US 7,217,127 B2
(45) Date of Patent: May 15, 2007

(54) SWITCHING DEVICE FOR IRRIGATION FLUIDS IN A DENTAL HANDPIECE

(75) Inventors: Dominique Mariaulle, Saint Aubin du Medoc (FR); Philippe Tichon, Mérignac (FR)

(73) Assignee: Societe Pour la Conception des Applications des Techniques Electroniques - Satelec, Merignac (FR)

( * ) Notice: Subject to any disclaimer, the term of this patent is extended or adjusted under 35 U.S.C. 154(b) by 157 days.

(21) Appl. No.: 10/506,470

(22) PCT Filed: Mar. 4, 2003

(86) PCT No.: PCT/FR03/00684

§ 371 (c)(1),
(2), (4) Date: Sep. 3, 2004

(87) PCT Pub. No.: WO03/073953

PCT Pub. Date: Sep. 12, 2003

(65) Prior Publication Data

US 2005/0255426 A1   Nov. 17, 2005

(30) Foreign Application Priority Data

Mar. 7, 2002   (FR) .................................. 02 02898

(51) Int. Cl.
*A61C 1/00*   (2006.01)
*F16K 11/02*   (2006.01)

(52) U.S. Cl. .............................. 433/98; 433/84; 251/6; 137/636.1

(58) Field of Classification Search .................. 433/98, 433/80, 84; 251/6; 137/636.1
See application file for complete search history.

(56) References Cited

U.S. PATENT DOCUMENTS

| 2,985,192 | A | * | 5/1961 | Taylor et al. | ............. 137/627.5 |
| 3,578,885 | A | * | 5/1971 | Alton | ......................... 417/454 |
| 3,823,724 | A |   | 7/1974 | Davis | |
| 3,918,490 | A | * | 11/1975 | Goda | ......................... 137/597 |
| 4,061,142 | A |   | 12/1977 | Tuttle | |
| 4,148,143 | A |   | 4/1979 | Fleer | |
| 4,168,707 | A | * | 9/1979 | Douvas et al. | ................. 604/32 |
| 4,259,985 | A | * | 4/1981 | Bergmann | ................... 137/595 |
| 4,328,834 | A | * | 5/1982 | Oates, Sr. et al. | ........ 137/636.1 |
| 4,484,599 | A | * | 11/1984 | Hanover et al. | ......... 137/636.1 |

(Continued)

FOREIGN PATENT DOCUMENTS

EP        1 243 225        9/2002

(Continued)

*Primary Examiner*—Ralph A. Lewis
(74) *Attorney, Agent, or Firm*—Young & Thompson

(57) ABSTRACT

A switching device for an irrigation line includes two flexible supply tubes (4*a*, 4*b*), each of the tubes connecting a flask containing an irrigation fluid to a handpiece via a peristaltic pump. The device includes at least one compression element (34*a*, 34*b*) and control members (32) which can apply the compression element alternatively to each of the flexible supply tubes (4*a*, 4*b*) in such a way as to squeeze and block the tube. The control members (32) are designed such that, when one of the tubes is being squeezed in order to block the passage of the fluid through same, the other tube is not being squeezed so that the fluid can flow through the other tube.

7 Claims, 2 Drawing Sheets

U.S. PATENT DOCUMENTS

| | | | |
|---|---|---|---|
| 4,585,442 A * | 4/1986 | Mannes ........................ | 604/250 |
| 4,702,733 A * | 10/1987 | Wright et al. .................. | 604/34 |
| 4,962,372 A | 10/1990 | Swier | |
| 5,113,906 A | 5/1992 | Högner | |
| 5,188,334 A * | 2/1993 | Yoshii et al. ................... | 251/7 |
| 5,199,604 A | 4/1993 | Palmer et al. | |
| 5,643,304 A * | 7/1997 | Schechter et al. .......... | 606/171 |
| 5,733,117 A * | 3/1998 | Coss et al. .................... | 433/85 |
| 6,589,197 B1 * | 7/2003 | Doi et al. ..................... | 604/6.1 |
| 2002/0162590 A1 * | 11/2002 | Lamas et al. ................ | 137/595 |

FOREIGN PATENT DOCUMENTS

FR        2 735 014        12/1996

* cited by examiner

SWITCHING DEVICE FOR IRRIGATION FLUIDS IN A DENTAL HANDPIECE

FIELD OF THE INVENTION

The present invention relates to a device ensuring the supply of a dental handpiece with two respective irrigation liquids.

BACKGROUND OF THE INVENTION

It is known that, during certain interventions, it is advantageous for a practitioner to have the possibility of supplying his handpiece alternately with different irrigation liquids.

In the devices of the prior state of the art, the "irrigation lines", i.e. the flexible tubes which connect the storage flasks to the handpiece via a peristaltic pump, are provided with a switching valve making it possible to connect the inlet of the pump successively to each of the flasks containing various irrigation liquids.

It will be understood that, in such devices, the irrigation line assembly cannot be of disposable type, unless the switching means are discarded with it, which, due to the costs involved, is difficult to envisage.

In certain devices of the prior state of the art, only that part of the irrigation line constituted by the flexible tubes is disposable, the switching means remaining, for their part, fast with the control apparatus. It will be understood that, under these conditions, the exchange of this disposable part of the irrigation line does not solve the problem of the sterility of the overall line.

OBJECTS OF THE INVENTION

The present invention has for its object to propose a device for controlling the switching of the irrigation line supplying a handpiece towards two respective flasks, which is such that it is isolated from the irrigation liquids so that the exchange of solely the flexible part of this irrigation line solves the problem of the sterility of the whole of the device.

The present invention thus has for its object a switching device for an irrigation line constituted by two flexible supply tubes, each connecting a flask containing an irrigation liquid to a handpiece by means of a peristaltic pump, characterized in that it comprises at least one compression element and control means which can apply this compression element alternately on each of the flexible supply tubes in such a way as to squeeze and block it, the control means being such that, when one of the tubes is being squeezed in order to block the passage of the liquid in this flexible tube, the other tube is not being squeezed so as to allow the liquid to flow in this other tube.

SUMMARY OF THE INVENTION

In one form of embodiment, the device according to the invention comprises two compression elements and the control means are adapted to apply each of these compression elements respectively on each of the flexible supply tubes so as to squeeze it and ensure blocking thereof, the control means being such that, when one of the compression elements is released, thus allowing the flow of the liquid in the corresponding tube, the other compression element is already squeezed so as to block the passage of the liquid in the other flexible tube.

In another form of embodiment of the invention, the control means are constituted by a sliding element which the user can actuate and which comprises two stops arranged at its respective ends, each stop being capable of occupying two positions, namely a position of blocking in which it compresses the flexible tube on a counter-stop, so as to squeeze it and block it, and a position of flow in which it does not apply the tube on the counter-stop and does not block it. The stops may be disposed in such a manner on the sliding element that, during the movement of displacement thereof, from one position to the other, one of the stops is located in position of blocking before the other stop is in position of flow.

According to the invention, the sliding element may be mounted mobile in rotation on a support pin so as to be able to pivot thereabout and occupy two positions, namely a position of functioning in which at least one compression element ensures squeezing of a tube, and a position of rest in which the compression elements are disengaged from the two tubes.

In a variant embodiment of the invention, the control means may be constituted by a rotating element comprising two cam elements adapted, during rotation of the rotating element, to come into abutment on one of the flexible tubes in order to compress it and squeeze it so as to ensure blocking thereof, each cam element being disposed so that, when one of the cams compresses a flexible tube to compress it and block it, the other cam is not in abutment on the other flexible tube so that the irrigation liquid can circulate therein.

The control means may equally well be constituted by at least one electromagnet controlling the displacement of at least one compression element adapted to compress one of the flexible tubes while releasing the other.

The present invention also has for an object a device for supplying a dental handpiece with two irrigation liquids employing a switching device, and a peristaltic pump, characterized in that the latter is of the expansion type.

The present invention also has for an object a device for supplying a dental handpiece employing a switching device, and a peristaltic pump driven by a motor, characterized in that the motor is a stepping motor.

BRIEF DESCRIPTION OF THE DRAWINGS

Various forms of embodiment of the present invention will be described hereinafter by way of non-limiting examples, with reference to the accompanying drawings, in which.

DETAILED DESCRIPTION OF THE INVENTION

Figure 1:
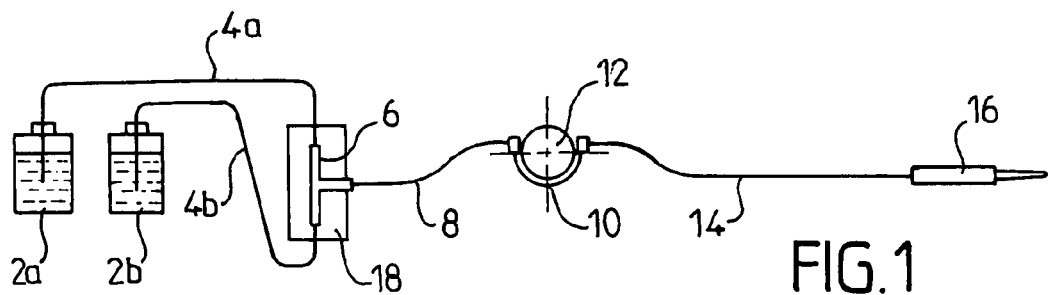
FIG. 1 is a general schematic view showing the different essential elements constituting an irrigation line.

FIG. 1 schematically shows an irrigation assembly. This assembly is constituted by two flasks 2a, 2b containing two respective irrigation liquids which are in communication by two flexible tubes 4a and 4b with the respective ends of the transverse branches of a T-shaped distributor 6. The central branch of the distributor 6 is connected, by a flexible tube 8, to the inlet of a tube element 10 of a peristaltic pump 12 of which the outlet is connected, by a flexible tube 14, to a handpiece 16. Switching means 18 are provided, allowing the flexible tube 8 to be placed in communication either with the flask 2a or with the flask 2b.

FIGS. 2 to 7 show a first form of embodiment of a switching device according to the invention.

This device is essentially constituted by a support plate 20 which comprises guides 22 which are intended to ensure positioning and maintenance in place of the distributor 6 on the transverse branches thereof, to which the flexible tube 4a connected to the first flask 2a and the flexible tube 4b connected to the second flask 2b are respectively connected. The central branch of the distributor 6 is connected, as shown in FIG. 1, to the tube 8 in communication with the inlet of the peristaltic pump 12.

On either side of the positioning guides 22, the support plate 20 comprises stops 24a and 24b on which the flexible tubes 4a and 4b come respectively into abutment. The support plate 20 also comprises two transverse bearings 26 in which a metal pin 28 is mounted to slide. This pin ensures the maintenance, at each of its ends, of two lugs 30 for maintaining a cover 32. The length l of the pin 28 is greater than the distance between two bearings 26, so that the cover 32 supported by the two support lugs 30 may effect a movement of translation along axis xx' of the two bearings 26, and this with an amplitude e equal to the difference in length existing between the length l of the pin 28 and the distance between the bearings 26.

Figure 6:
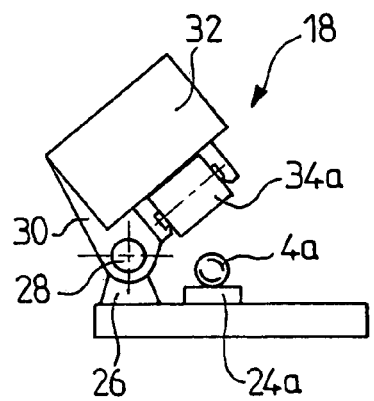
FIGS. 6 and 7 are schematic side views representing the switching device, on the one hand in position of placing the supply tubes in position therein, and, on the other hand, in the course of functioning.
Figure 7:
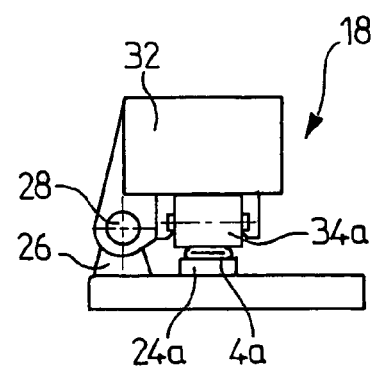
Figure 5:
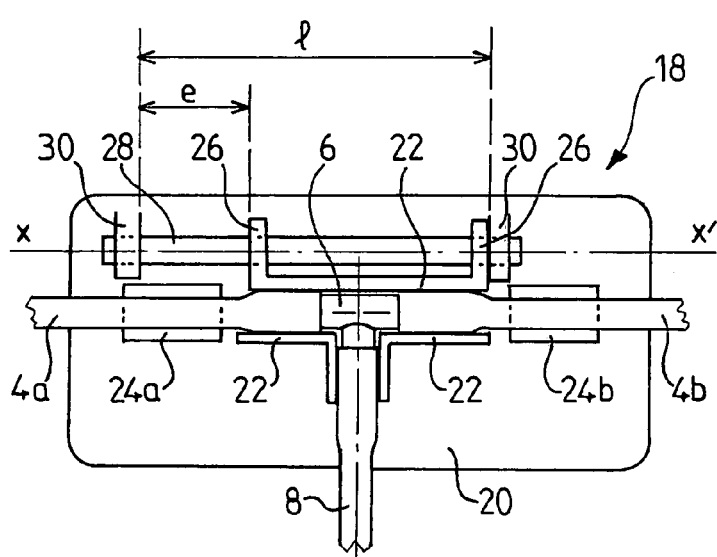
FIG. 5 is a partial plan view of the switching device shown in FIG. 3.

In addition to its longitudinal movement of translation, along axis xx', the cover 32 can also effect a movement of rotation about axis 28, which allows it to occupy, as shown in FIGS. 6 and 7 respectively, two respective positions, namely a first, raised position (FIG. 6), which corresponds to a position of placing the distributor 6 in position in the positioning guides 22, and a second, lowered position or position of functioning (FIG. 7).

The cover 32 comprises at its ends respective rollers 34a and 34b which are arranged so that, when the cover 32 is in position of functioning (lowered position), as shown in FIGS. 2, 3, 4 and 7, the rollers 34a and 34b squeeze the respective flexible tubes 4a and 4b by applying them on the stops 24a and 24b and deform them so as to ensure their total blocking, which prevents the passage of the irrigation liquids coming from the tubes 4a and 4b towards the tube 8.

Figure 2:
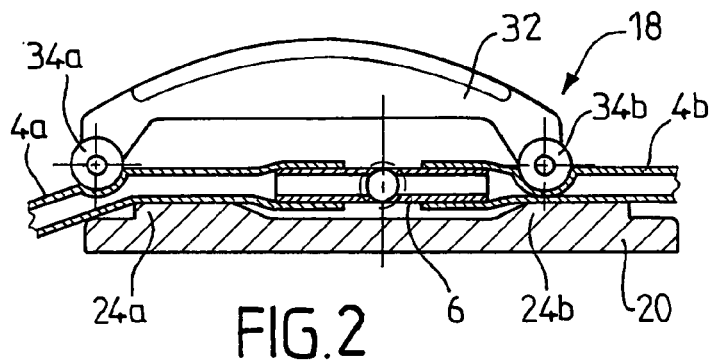
FIG. 2 is a view in vertical and longitudinal section of a first form of embodiment of a switching device according to the invention, ensuring the blocking of one of the two tubes supplying irrigation liquid to a handpiece.

The cover 32 may occupy two extreme longitudinal positions, namely a first position, shown in FIG. 2, in which the roller 34b compresses the flexible tube 4b and squeezes it against the stop 24b, so that it ensures blocking of this tube. In this same position, the roller 34a is not located opposite the stop 24a, so that it does not squeeze the flexible tube 4a sufficiently to block it, with the result that the irrigation fluid coming from the flask 2a is in communication, via the switching means 18, with the flexible tube 8 connected to the peristaltic pump 12.

Figure 3:
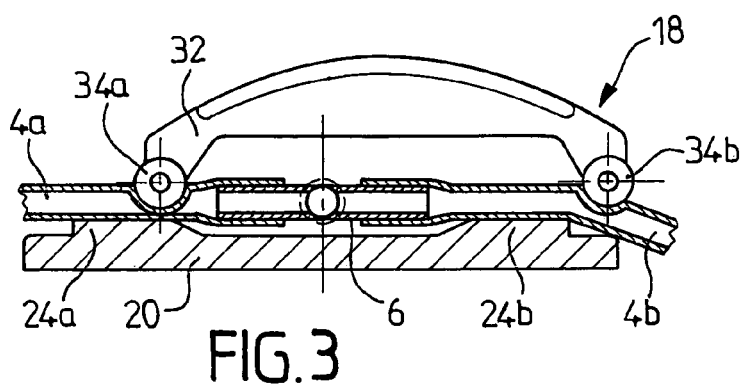
FIG. 3 is a view identical to that of FIG. 2, in which the switching device ensures the blocking of the other tube supplying irrigation liquid.
Figure 4:
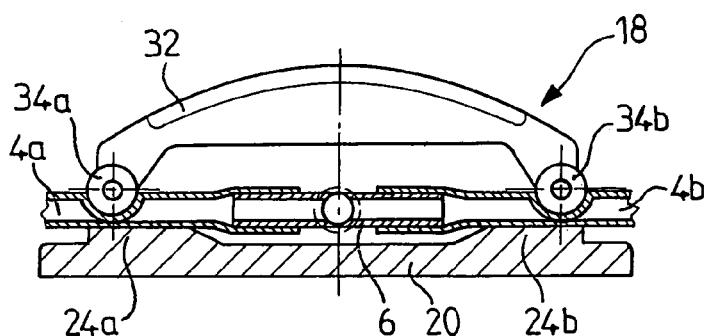
FIG. 4 is a view identical to the preceding ones in which the switching device ensures the blocking of the two tubes supplying irrigation liquid.

When the cover 32 is displaced by translation into its other extreme position, shown in FIG. 3, it is in that case the flexible tube 4a which is squeezed and blocked by the roller 34a and the flexible tube 4b which is not squeezed by the roller 34b and which is therefore not blocked, with the result that the irrigation liquid contained in the flask 2b is in communication with the flexible tube connected to the peristaltic pump 12.

Such a devices proves to be particularly interesting when it is desired that at no moment it be possible for the two irrigation liquids to be able to be mixed and supplied to the tube 8.

However, in one embodiment of the invention, it would, of course, be possible, if such were of interest to the practitioner, to move the stops 24a and 24b apart from each other so that, under these conditions, it would then be possible to supply to the tube 8 in communication with the peristaltic pump 12 a mixture of irrigation liquids 2a and 2b distributed in a proportion depending on the longitudinal position of the cover 32.

The present device is also particularly interesting insofar as the switching means are completely independent of the irrigation line, with the result that the latter may, at lower cost, constitute a disposable element, this presenting the advantage of solving the problems of asepsis.

Another advantage of the switching device according to the invention is that, as may be seen in FIGS. 2 and 3, the cover is displaced, constituting the control of switching in the direction of the tube which it is desired to have supplied with irrigation liquid, this representing, for the practitioner, a pleasure to use.

The switching means may, of course, be constituted by any other means ensuring compression and blocking of one of the supply tubes while ensuring opening of the other.

Figure 8:
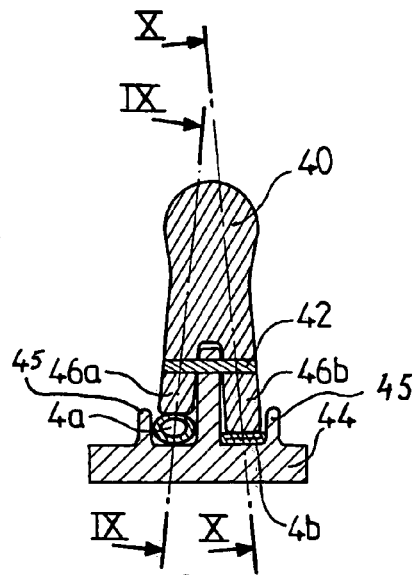
FIG. 8 is a schematic view in vertical and transverse section of a variant embodiment of the switching device according to the invention.
Figure 9:
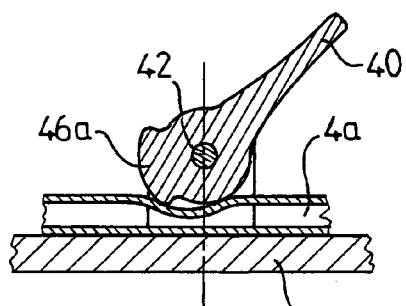
FIGS. 9 and 10 are views in longitudinal section of the switching device shown in FIG. 8, along lines IX—IX and X—X thereof, respectively.
Figure 10:
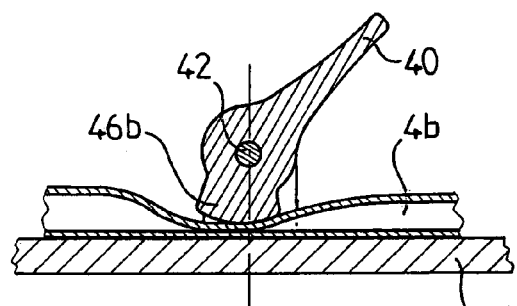

Devices employing rotary control means might for example be used, as is schematically shown in FIGS. 8 to 10.

The rotating switching device shown in these Figures is essentially constituted by a lever 40 mounted to rotate about a horizontal pin 42 fast with a support plate 44. This support plate comprises two longitudinal guides 45 which respectively receive the two flexible supply tubes 4a and 4b respectively connected to the two flasks 2a and 2b. The lower part of the lever 40 is divided into two substantially parallel cams 46a and 46b respectively disposed above the guides of the flexible tubes 4a and 4b arranged so that, for one of the extreme positions that the lever 40 can occupy, one of the cams compresses one of the flexible tubes, while the other cam does not compress the other tube. In this way, the Figures have shown the lever 40 in an extreme position in which its cam 46a does not compress the tube 4a (FIG. 9), while, in this same position, the other cam 46b squeezes the other flexible tube 4b (FIG. 10) so as to block it. It will thus be understood that, in each of these characteristic extreme positions, the lever 40 blocks one of the flexible tubes while it does not block the other tube.

Any other means might, of course, be used, particularly electrical or electromechanical means, for compressing one of the flexible tubes so as to block it and, at the same time, release the other tube so as to allow the irrigation liquid to flow therein.

Figure 11:
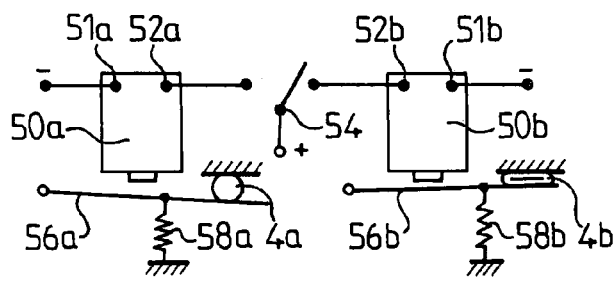
FIG. 11 is a schematic variant of electromechanical means for controlling this device.

As shown in FIG. 11, two electromagnets, 50a and 50b respectively, might for example be employed, of which one of the supply terminals 51a and 51b is connected to earth while the other terminal 52a and 52b is connected to the other current supply terminal via a two-position reversing switch 54. Each electromagnet, when it is supplied, attracts a pivoting lever, 56a, 56b respectively, which compresses one of the flexible tubes in order to squeeze it and block it, against a return effort exerted by a spring 58a, 58b respectively. It will thus be understood that, as a function of the position of the reversing switch 54, one or the other of the two flexible tubes will be blocked.

Figure 11A:
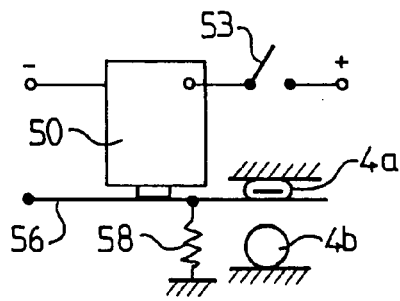
FIG. 11a is a variant embodiment of FIG. 11.

As shown in FIG. 11a, one sole electromagnet 50 may also be employed, of which the current supply is controlled by a switch 53 and which, when it is supplied, attracts a lever 56 which squeezes one of the tubes 4a against the force exerted by a return spring 58, and which, when it is not supplied, releases the lever 56 which, under the action of the spring 58, then compresses the other tube 4b and blocks it.

Figure 12:
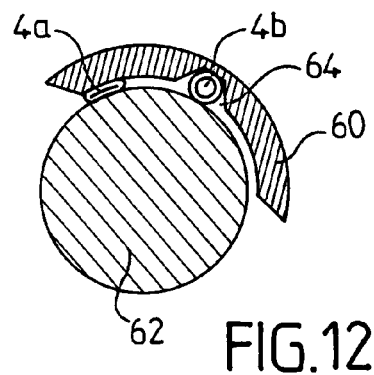
FIG. 12 is a schematic view in transverse section of another variant embodiment of the switching device according to the invention.

As schematically shown in FIG. 12, one or the other of the flexible supply tubes 4a and 4b might also be compressed with the aid of a rotating element 60 applying on the cylindrical body of a handpiece 62 each of the flexible tubes, a hollow 64 being provided on the inner face of the rotating element 60 so, as a function of its position, as to receive one or the other of the two tubes which, in this way, will not be blocked. Such a device is particularly interesting in that it can be easily disposed on a dental handpiece.

In a form of embodiment of the present invention, the peristaltic pump 12 will preferably be of the expansion type. The pumps of this type are particularly advantageous insofar as they do not have a stator but a runway in which is squeezed a flexible tube under the action of rollers fast with the rotor. Such an embodiment presents the advantage of double simplicity, both from the standpoint of manufacture and from that of use.

The peristaltic pump may be driven by a stepping motor which, while delivering a sufficient rotary torque to allow it to perform its function of compression of the tube element 10, will allow a disengaging of the motor without calling upon an annexed mechanical disengagement device if phenomena of blocking of the pump occur. Such an arrangement of the pump is particularly advantageous from the standpoint of security, thus allowing it to be disposed so that the user can have immediate access to the system for positioning the part 10 of the irrigation tube.

The other switching means might, furthermore, be adapted in order to dispose them on the handpiece.

The invention claimed is:

1. Switching device comprising:
 a support (20) provided with positioning guides (22) defining a first location adapted to receive a first inlet flexible tube, a second location adapted to receive a second inlet flexible tube and a third location adapted to receive an outlet flexible tube, said support being further provided with a first stop (24a) and a second stop (24b) within the first and second locations respectively, and
 a cover (32) comprising two compression elements (34a, 34b), each compression element being adapted selectively to squeeze an inlet flexible tube against a stop, when an inlet flexible tube is in the first or second location,
 wherein
 said first and second locations extend along a first axis, and
 said cover (32):
 is pivotable about an axis (x–x') parallel to said first axis, between a working position, in which the compression elements are facing the first and second locations, and a rest position, in which both compression elements are away from the first and second locations, and
 is slidable along said first axis, the compression elements being arranged such that at least one compression element is always facing a said stop.

2. Device according to claim 1, wherein each compression element is a roller.

3. Device according to claim 1, wherein the cover (32) is a sliding element adapted to be actuated by a user, the compression elements being at respective ends of said slidable element.

4. Device according to claim 1, wherein the compression elements are disposed on the cover such that, during a sliding movement of said cover, one of the two compression elements is facing a stop before the other compression element is away from the other stop.

5. Assembly for supplying a dental handpiece with two irrigation liquids, said assembly comprising a switching device according to claim 1, two flasks containing said irrigation liquids, first and second inlet flexible tubes (4a, 4b) between respective flasks and the switching device, a peristaltic pump (12) and an outlet tube (8) between the switching device and the peristaltic pump.

6. Assembly according to claim 5, which further comprises a stepping motor for driving the peristaltic pump.

7. Dental handpiece comprising a switching device according to claim 1.

* * * * *